US009463325B1

(12) United States Patent
Young et al.

(10) Patent No.: US 9,463,325 B1
(45) Date of Patent: Oct. 11, 2016

(54) SYSTEMS AND METHODS FOR MAINTAINING A BI-DIRECTIONAL COMMUNICATION BETWEEN AN IMPLANTABLE MEDICAL DEVICE AND AN EXTERNAL DEVICE

(71) Applicant: Pacesetter, Inc., Sunnyvale, CA (US)

(72) Inventors: Chao-Wen Young, Cupertino, CA (US); Germinal Ibarrola, Plano, TX (US); Yongjian Wu, Saratoga, CA (US); Mostafa Sadeghi, Los Angeles, CA (US); Erik Shreve, Dallas, TX (US); Andrew Rissing, McKinney, TX (US); Min Yang, Los Altos, CA (US); Jun Yang, Valencia, CA (US); Thanh Tieu, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 5 days.

(21) Appl. No.: 14/737,361

(22) Filed: Jun. 11, 2015

(51) Int. Cl.
*A61N 1/372* (2006.01)
*H04W 76/04* (2009.01)
*H04W 12/04* (2009.01)
*H04W 12/06* (2009.01)

(52) U.S. Cl.
CPC .......... *A61N 1/37217* (2013.01); *H04W 12/04* (2013.01); *H04W 12/06* (2013.01); *H04W 76/043* (2013.01)

(58) Field of Classification Search
None
See application file for complete search history.

(56) References Cited

U.S. PATENT DOCUMENTS

| 7,065,409 | B2 * | 6/2006 | Mazar | A61N 1/08 128/903 |
| 9,288,614 | B1 * | 3/2016 | Young | A61N 1/37252 |
| 9,289,614 | B2 * | 3/2016 | Wu | A61N 1/37252 |
| 2008/0103551 | A1 * | 5/2008 | Masoud | A61N 1/37276 607/59 |

* cited by examiner

*Primary Examiner* — Brian T Gedeon
(74) *Attorney, Agent, or Firm* — Theresa A. Raymer

(57) ABSTRACT

Systems and methods are provided for maintaining a bi-directional communication link between an external device and an implantable medical device (IMD). The systems and methods receive a connection request from an external device at the IMD. The communication request includes one or more communication link parameters based on a wireless protocol, defining a first communication interval. The systems and methods establish a bi-directional communication link between the external device and the IMD based on the one or more communication link parameters, and receive, during the first communication interval, a data packet from the external device along a first data channel, the data packet including an adjusted communication link parameter. The adjusted communication link parameter include a second communication interval.

20 Claims, 7 Drawing Sheets

SYSTEMS AND METHODS FOR MAINTAINING A BI-DIRECTIONAL COMMUNICATION BETWEEN AN IMPLANTABLE MEDICAL DEVICE AND AN EXTERNAL DEVICE

BACKGROUND OF THE INVENTION

Embodiments of the present disclosure generally relate to systems and methods for a bi-directional communication link between devices, and more particularly for maintaining bi-directional communication between an implantable medical device and an external device.

An implantable medical device ("IMD") is a medical device that is configured to be implanted within a patient anatomy and commonly employs one or more leads with electrodes that either receive or deliver voltage, current or other electromagnetic pulses (generally "energy") from or to an organ or tissue for diagnostic or therapeutic purposes. In general, IMDs include a battery, electronic circuitry, such as a pulse generator and/or a microprocessor that is configured to handle RF communication with an external device as well as control patient therapy. The components of the IMD are hermetically sealed within a metal housing (generally referred to as the "can").

IMDs are programmed by and transmit data to external devices controlled by physicians and/or the patient. The external devices communicate by forming wireless bi-directional communication links with the IMDs. Recently, the IMD may communicate with the external device using commercial protocols such as Bluetooth Low Energy (BLE), which are compatible with commercial wireless devices such as tablet computers, smartphones, and the like. Commercial protocols include several default security mechanisms, such as a frequency hopping algorithm, which change frequencies of subsequent data packets for predetermined communication intervals. However, many of these security mechanisms are based on publicly available wireless protocol specifications, and are implemented using information exchanged between the devices before or prior to communication being encrypted, thereby allowing information exchanged between the devices to be susceptible to packet analyzers or packet sniffers.

Packet sniffers are programs and/or computer hardware designed to intercept and/or log wireless traffic (e.g., transmission of data packets) over a wireless network to eavesdrop or intrude on communications between two devices (e.g., the IMD and an external device). Packet sniffers may capture one or more data packets and decode the one or more data packets determining values of various fields within the data packet. Further, the packet sniffer can analyze content of the various fields according to the wireless protocol specification.

For example, the frequency hopping algorithm is predefined using a connection request packet that includes information based on a specification of the commercial protocol. The packet sniffer can capture and use the information from the connection request packet to frequency hop concurrently with the IMD and the external devices. Thereby, the packet sniffer may follow the frequency hops between the IMD and the external device acquiring one or more of the transmitted data packets transmitted between the devices. Further, the packet sniffer may reuse or replay captured data packets to interrupt communication with the IMD and/or the external device. Additionally, the packet sniffer may reuse and adjust the captured data packets for "man in the middle" attacks on the IMD and/or the external device. Thus, a need exists for improved methods and systems for securing bi-directional communication between the IMD with the external device.

BRIEF SUMMARY

In accordance with an embodiment herein, a method is provided for maintaining a bi-directional communication link between an external device and an implantable medical device (IMD). The method receives a connection request from an external device at an IMD. The communication request includes one or more communication link parameters based on a wireless protocol. The one or more communication link parameters defining a first communication interval. The method also includes establishing a bi-directional communication link between the external device and the IMD based on the one or more communication link parameters. The method also includes receiving, during the first communication interval, a data packet from the external device along a first data channel, the data packet including an adjusted communication link parameter. The adjusted communication link parameter includes a second communication interval having a length that is different from a length of the first communication interval.

In an embodiment, a system for maintaining a bi-directional communication link is provided. The system includes an external device and an implantable medical device (IMD) configured to establish a bi-directional communication link there between over a wireless protocol. The bi-directional communication link is based on one or more communication link parameters, at least one of which is a communication interval and a data channel map. The IMD includes one or more processors electrically coupled to a radio frequency (RF) circuit and a memory. The one or more processors are configured to continuously shift the RF circuit to select data channels from the data channel map at the communication interval. The one or more processors are further configured to receive an adjusted communication link parameter from the external device. The adjusted communication link parameter includes at least a second communication interval. A length of the second communication interval is different from the communication interval. The one or more processors are further configured to adjust the communication interval to the second communication interval.

DETAILED DESCRIPTION

Figure 1:
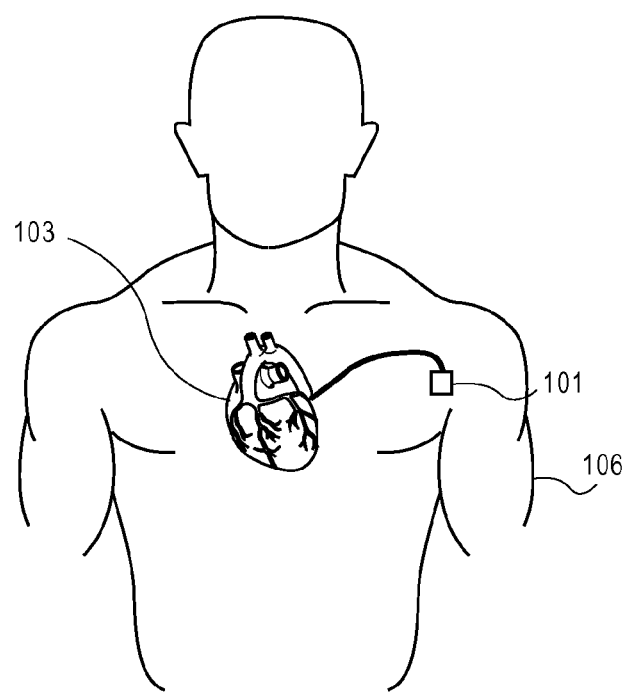
FIG. 1 illustrates simplified block diagram of a system for initiating a bi-directional communication link, according to an embodiment of the present disclosure.
Figure 1:
Figure 1:
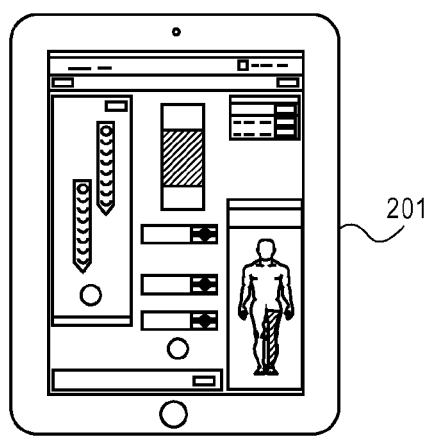

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Various embodiments described herein include a method and/or system for a secure bi-directional communication link between an external device and an implantable medical device (IMD). The bi-directional communication link may be based on one or more communication link parameters. The one or more communication link parameters may correspond to various connection parameters (e.g., communication interval, frequency, address, transmit windows, timeout parameters, cyclic redundancy check) that define the bi-directional communication link based on a wireless protocol such as Bluetooth Low Energy (BLE), Bluetooth, ZigBee, or the like. The one or more communication link parameters are transmitted to the IMD and/or the external device within a connection request to establish the bi-directional communication link during a bonding or pairing procedure defined by the wireless protocol.

Once the bi-directional communication link is established, the IMD and external device may alternate sending and receiving data packets during communication intervals. After each of the communication intervals, the external device and the IMD may move and/or shift to another frequency channel derived from a frequency hopping algorithm based on a data channel map and a frequency hopping increment within the connection request.

Various embodiments described herein may adjust at least one of the communication link parameters after the bonding and/or pairing procedure is complete as defined by the wireless protocol (e.g., transmit data packets along a data channel). For example, the IMD may request a communication link parameter update from the external device. The external device may transmit an adjusted communication link parameter, such as, an adjusted communication interval, an adjusted frequency hopping increment, and/or the like.

Additionally or alternatively, various embodiments described herein may affix or include a session authenticity message within payloads of data packets transmitted in the bi-directional communication link. The session authenticity message may be a message authentication guard (MAG). The IMD and/or the external device may use the MAG to check the validity of the received data packet, and proceed with responding and/or executing an instruction based on the data packet when the MAG is validated.

In various embodiments the MAG may be based on a symmetric cipher scheme or an asymmetric cipher scheme as further described herein. The size and/or complexity of the MAG may be dependent on the overall system performance of the IMD and/or the external device. For example, an IMD with a high system performance may use a MAG corresponding to a dynamic value that may change after one or more transmissions from the IMD during the bi-directional communication link. In another example, for an IMD with a low system performance, the IMD may calculate a MAG corresponding to a static value that does not change during the bi-directional communication link. Thereby, reducing an amount of processing by the IMD during the bi-directional communication link relative to the IMD calculating the MAG corresponding to the dynamic value.

A technical effect of the various embodiments herein mitigate effects of packet sniffing attacks such as man in the middle, message replay attacked, and/or the like. A technical effect of the various embodiments herein may reduce a number of data packets that may be monitored and/or captured by an unauthorized device. A technical effect of the various embodiments herein provide additional security features such as adjusting communication link parameters and/or MAG to wireless protocols, for example Bluetooth Low Energy (BLE).

FIG. 1 illustrates a simplified block diagram of a system for maintaining a secure bi-directional communication link between an external device 201 and an implantable medical device (IMD) 101. The external device 201 may represent a table computer, smart phone, laptop, or the like. The external device 201 may program the IMD 101 and/or receive data from the IMD 101 via the bi-directional communication link 104. For example, the external device 201 may transmit a request for data measurements. The request is received by the IMD 101, and in response to the request, the IMD 101 may transmit the measurements to the external device 201 over the bi-directional communication link 104. The bi-directional communication link 104 may use any standard wireless protocol such as BLE, Bluetooth, Wireless USB, Medical Implant Communication Service, ZigBee, and/or the like that define a means for transmitting and receiving information (e.g., data, commands, instructions) between devices.

The IMD 101 may be implanted within the patient 106 (e.g., proximate to a heart 103, proximate to the spinal cord). Additionally or alternatively, the IMD 101 may have components that are external to the patient 106, for example, the IMD 101 may include a neuro external pulse generator (EPG). The IMD 101 may be one of various types of implantable devices, such as, for example, a leadless pacemaker, neurostimulator, electrophysiology (EP) mapping and radio frequency (RF) ablation system, an implantable pacemaker, implantable cardioverter-defibrillator (ICD), defibrillator, cardiac rhythm management (CRM) device, an implantable pulse generator (IPG), or the like.

Figure 2:
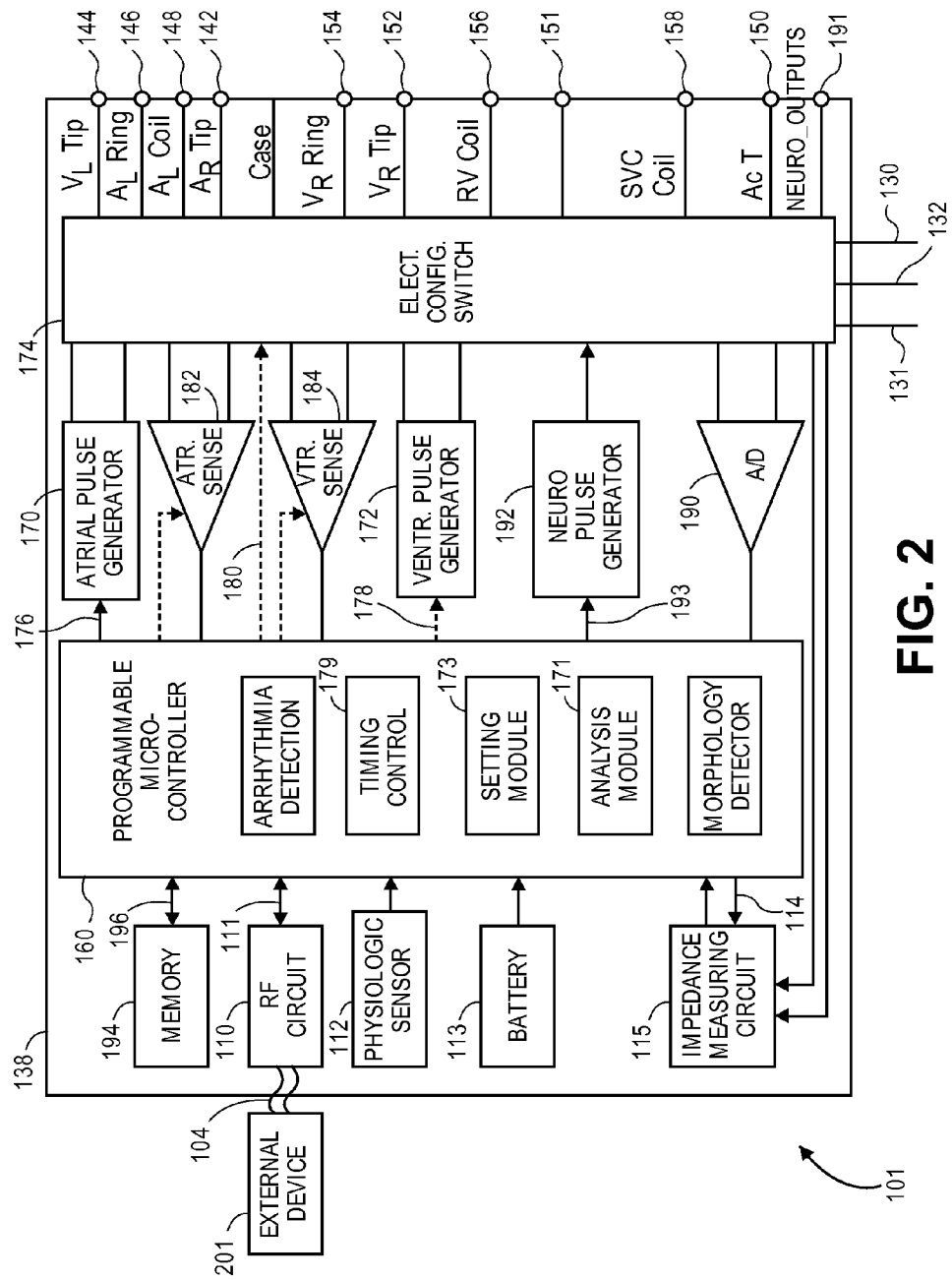
FIG. 2 illustrates a block diagram of exemplary internal components of an implantable medical device, according to an embodiment of the present disclosure.

FIG. 2 illustrates a block diagram of exemplary internal components of the IMD 101. The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

The IMD 101 is for illustration purposes only, and it is understood that the circuitry could be duplicated, eliminated or disabled in any desired combination to provide a device capable of treating the appropriate chamber(s) with cardioversion, defibrillation and/or pacing stimulation as well as providing for apnea detection and therapy. Additionally or alternatively, the IMD 101 may be used to generate electrical stimulation for application to a desired area of a body, such as a spinal cord stimulation, as described later herein corresponding to FIG. 9.

The housing 138 for the IMD 101, shown schematically in FIG. 2, is often referred to as the "can", "case" or "case electrode" and may be programmably selected to act as the return electrode for all "unipolar" modes. The housing 138 may further be used as a return electrode alone or in combination with one or more of the coil electrodes for shocking purposes. The housing 138 further includes a connector (not shown) having a plurality of terminals, 142, 152, 154, 156 and 158 (shown schematically and, for convenience, the names of the electrodes to which they are connected are shown next to the terminals. A right atrial tip terminal ($A_R$ TIP) 142 is adapted for connection to the atrial tip electrode and a right atrial ring terminal may be adapted for connection to right atrial ring electrode. A left ventricular tip terminal ($V_L$ TIP) 144, a left atrial ring terminal ($A_L$ RING) 146, and a left atrial shocking terminal ($A_L$ COIL) 148 are adapted for connection to the left ventricular ring electrode, and a left atrial tip electrode and a left atrial coil electrode respectively. A right ventricular tip terminal ($V_R$ TIP) 152, a right ventricular ring terminal ($V_R$ RING) 154, a right ventricular shocking terminal ($R_V$ COIL) 156, and an SVC shocking terminal (SVC COIL) 158 are adapted for connection to the right ventricular tip electrode, right ventricular ring electrode, an RV coil electrode, and an SVC coil electrode, respectively.

An acoustic terminal (ACT) 150 is adapted to be connected to an external acoustic sensor or an internal acoustic sensor, depending upon which (if any) acoustic sensors are used. Terminal 151 is adapted to be connected to a blood sensor to collect measurements associated with glucose levels, natriuretic peptide levels, or catecholamine levels.

The IMD 101 includes a programmable microcontroller 160 which controls operation. The microcontroller 160 (also referred to herein as a processor module or unit) typically includes a one or more processors or microprocessors, or equivalent control circuitry, designed specifically for controlling the delivery of stimulation therapy and may further include RAM or ROM memory, logic and timing circuitry, state machine circuitry, and I/O circuitry. Typically, the microcontroller 160 includes the ability to process or monitor input signals (data) as controlled by program code stored in memory. The details of the design and operation of the microcontroller 160 are not critical to the invention. Rather, any suitable microcontroller 160 may be used that carries out the functions described herein. Among other things, the microcontroller 160 receives, processes, and manages storage of digitized cardiac data sets from the various sensors and electrodes. For example, the cardiac data sets may include IEGM data, pressure data, heart sound data, and the like.

The IMD 101 includes an atrial pulse generator 170 and a ventricular/impedance pulse generator 172 to generate pacing stimulation pulses for delivery by the right atrial lead 130, the right ventricular lead 131, and/or the coronary sinus lead 132 via an electrode configuration switch 174. It is understood that in order to provide stimulation therapy in each of the four chambers of the heart, the atrial and ventricular pulse generators, 170 and 172, may include dedicated, independent pulse generators, multiplexed pulse generators or shared pulse generators. The pulse generators, 170 and 172, are controlled by the microcontroller 160 via appropriate control signals, 176 and 178, respectively, to trigger or inhibit the stimulation pulses.

The IMD 101 may include a neuro stimulation pulse generator circuit 192 to generate stimulation pulses for a brain or spinal cord nervous system. The stimulation pulses are delivered by a plurality of electrodes through the neuro output lead 191. The neuro stimulation pulse generator circuit 192 is controlled by the microcontroller 160 via appropriate control signals 193 to trigger or generate the stimulation pulses.

The microcontroller 160 further includes timing control circuitry 179 used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 174 includes a plurality of switches for connecting the desired electrodes to the appropriate I/O circuits, thereby providing complete electrode programmability. Accordingly, the switch 174, in response to a control signal 180 from the microcontroller 160, determines the polarity of the stimulation pulses (e.g., unipolar, bipolar, etc.) by selectively closing the appropriate combination of switches (not shown) as is known in the art.

Atrial sensing circuit 182 and ventricular sensing circuit 184 may also be selectively coupled to the right atrial lead 130, coronary sinus lead 132, and the right ventricular lead 131, through the switch 174 for detecting the presence of cardiac activity in each of the four chambers of the heart. Accordingly, the atrial (ATR SENSE) and ventricular (VTR SENSE) sensing circuits, 182 and 184, may include dedicated sense amplifiers, multiplexed amplifiers or shared amplifiers. The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

Cardiac signals are also applied to the inputs of an analog-to-digital (A/D) data acquisition system 190. The data acquisition system 190 is configured to acquire IEGM signals, convert the raw analog data into a digital IEGM signal, and store the digital IEGM signals in memory 194 for later processing and/or RF transmission along the bi-directional communication link 104. The data acquisition system 190 is coupled to the right atrial lead 130, the coronary sinus lead 132, and the right ventricular lead 131 through the switch 174 to sample cardiac signals across any combination of desired electrodes. The data acquisition system 190 may also be coupled, through switch 174, to one or more of the acoustic sensors. The data acquisition system 190 acquires, performs A/D conversion, produces and saves the digital pressure data, and/or acoustic data.

The controller 160 includes an analysis module 171 and a setting module 173 that function in accordance with embodiments described herein. The analysis module 171 analyzes a characteristic of interest from the heart. The level of the characteristic changes as the pacing parameter is changed. The setting module 173 sets a desired value for the pacing parameter based on the characteristic of interest from the heart. The pacing parameter may represent at least one of an AV delay, a VV delay, a VA delay, intra-ventricular delays, electrode configurations and the like. The controller 160 changes at least one of the AV delay, the VV delay, the VA delay, the intra-ventricular delays, electrode configurations and like in order to reduce systolic turbulence and regurgitation.

The RF circuit 110 may be configured to handle and/or manage the bi-directional communication link between the IMD 101 and the external device 201. The RF circuit 110 may be electrically coupled to the microcontroller 160. The RF circuit 110 is controlled by the microcontroller 160 and may support a particular wireless communication protocol while communicating with the external device 201, such as BLE, Bluetooth, ZigBee, Medical Implant Communication Service (MICS), or the like. Protocol firmware may be stored in memory 194, which is accessed by the microcontroller 160. The protocol firmware provides the wireless protocol syntax for the controller 160 to assemble data packets, establish communication links 104, and/or partition data received from the external device 201.

The microcontroller 160 is electrically coupled to memory 194 by a suitable data/address bus 196, wherein the programmable operating parameters used by the microcontroller 160 are stored and modified, as required, in order to customize the operation of IMD 101 to suit the needs of a particular patient. The memory 194 also stores data sets (raw data, summary data, histograms, etc.), such as the IEGM data, heart sound data, pressure data, Sv02 data and the like for a desired period of time (e.g., 1 hour, 24 hours, 1 month). The memory 194 may be a non-transitory computer readable medium such as RAM, ROM, EEPROM, a hard drive, or the like. The memory 194 may store instructions to direct the microcontroller 160 to analyze the cardiac signals and heart sounds identify characteristics of interest and derive values for predetermined statistical parameters. The data stored in memory 194 may be selectively stored at certain time intervals, such as 5 minutes to 1 hour periodically or surrounding a particular type of arrhythmia of other irregularity in the heart cycle.

The memory 194 may include a pre-defined algorithm that generates a passkey. The passkey may be used during a pairing and/or bonding procedure between the IMD 101 and the external device 201 to establish the bi-directional communication link 104. The passkey may be generated based on connection identification information. The connection identification information may include a dynamic seed and/or a static identification or encrypted static identification transmitted by the RF circuit 110 through the bi-directional communication link 104 from the external device 201 and inputted into the pre-defined algorithm. Optionally, the dynamic seed may be a random number generated by the microcontroller 160, based on the local system clock of the IMD 101, or the like that is transmitted by the RF circuit 110 to the external device 201. Additionally or alternatively, the static identification may be stored on the memory 194 representing a product serial identification number of the IMD 101, which is a unique number assigned to the IMD 101 by a manufacturer of the IMD 101. Optionally, the static identification may be a pre-determined number stored on the memory 194 set by a user.

Additionally or alternatively, the memory 194 may include a pre-defined encryption algorithm to generate a public key and/or private key. The public key may be transmitted to another device, such as the external device, for calculating a message authentication guard (MAG). The public key may be generated by the microcontroller 160 based on the pre-defined encryption algorithm stored on the memory 194. The pre-defined encryption algorithm may be asymmetric based on an RSA algorithm standard (e.g., having key lengths of RSA-1024, RSA-2048, or the like), Digital Signature Algorithm, or the like. The public key may be mathematically linked with the private key, such that a MAG calculated with the public key may be verified or decrypted with the private key.

For example, the microcontroller 160 may generate a public key using the pre-defined encryption algorithm based on a private key stored on the memory 194. Optionally, the public key may be generated concurrently with or preceding to the generation of the private key by the microcontroller 160 using the pre-defined encryption algorithm. The public key is transmitted by the IMD 101 to the external device 201. The external device 201 may encrypt a pre-defined criteria based on the public key to generate or calculate a MAG to be attached to a data packet. The pre-defined criteria may be based on a time stamp, a static value, or a payload of the data packet and is known by the IMD 101 and the external device 201. The IMD 101 may receive the data packet from the external device 201 and decrypt the MAG using the private key and the pre-defined encryption algorithm. If the IMD 101 matches the pre-defined criteria, the IMD 101 may determine that the MAG is verified. It should be noted that in other embodiments the MAG may be calculated using the private key and verified or decrypted with the public key.

Additionally or alternatively, the MAG may be calculated and decrypted using a single private key in both the IMD 101 and the external device 201. For example, the pre-defined encryption algorithm may correspond to a symmetric-key based on an advanced encryption standard (AES), Salsa20, Threefish, or the like.

The pacing and other operating parameters of the IMD 101 may be non-invasively programmed into the memory 194 through the RF circuit 110 via the bi-directional communication link 104. The RF circuit 110 is controlled by the microcontroller 160 and receives data for transmission by an interconnect 111. The RF circuit 110 allows intra-cardiac electrograms, pressure data, acoustic data, Sv02 data, and status information relating to the operation of IMD 101 (as contained in the microcontroller 160 or memory 194) to be sent to the external device 201 through the established bi-directional communication link 104. The RF circuit 110 also allows new pacing parameters for the setting module 173 used by the IMD 101 to be programmed through the bi-directional communication link 104.

To establish the bi-directional communication link 104 between the external device 201 and the IMD 101, the microcontroller 160 may enter an advertisement mode by instructing the RF circuit 110 to transmit or broadcast one or more advertisement notices along a dedicated advertisement channel defined by the wireless protocol. The advertisement channel is a point to multipoint, unidirectional, channel to carry a repeating pattern of system information messages such as network identification, allowable RF channels to establish the bi-directional communication link 104, and/or the like that is included within the advertisement notice. The advertisement notice may be repeatedly transmitted after a set duration or an advertisement period until the bi-directional communication link 104 is established with the external device 201.

Optionally, the length of the advertisement period may be adjusted by the microcontroller 160 during a select advertisement mode. For example, during the select advertisement mode the microcontroller 160 may reduce the length of the advertisement period relative to not being in the select advertisement mode. The reduced length of the advertisement period results in the RF circuit 110 transmitting more or an increased number of advertisement notices relative to not being in the select advertisement mode.

The IMD 101 may also include a physiologic sensor 112, such as an accelerometer, commonly referred to as a "rate-responsive" sensor, to record the activity level of the patient or adjust pacing stimulation rate according to the exercise state of the patient. Optionally, the physiological sensor 112 may further be used to detect changes in cardiac output, changes in the physiological condition of the heart, or changes in activity (e.g., detecting sleep and wake states) and movement positions of the patient. While shown as being included within IMD 101, it is to be understood that the physiologic sensor 112 may also be external to the IMD 101, yet still be implanted within or carried by the patient. A common type of rate responsive sensor is an activity sensor incorporating an accelerometer or a piezoelectric crystal, which is mounted within the housing 138 of the IMD 101.

The physiologic sensor 112 may be used as the acoustic sensor that is configured to detect the heart sounds. For example, the physiologic sensor 112 may be an accelerometer that is operated to detect acoustic waves produced by blood turbulence and vibration of the cardiac structures within the heart (e.g., valve movement, contraction and relaxation of chamber walls and the like). When the physiologic sensor 112 operates as the acoustic sensor, it may supplement or replace entirely acoustic sensors. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 101 additionally includes a battery 113, which provides operating power to all of the circuits shown. The IMD 101 is shown as having impedance measuring circuit 115 which is enabled by the microcontroller 160 via a control signal 114. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 115 is advantageously coupled to the switch 174 so that impedance at any desired electrode may be obtained.

Figure 3:
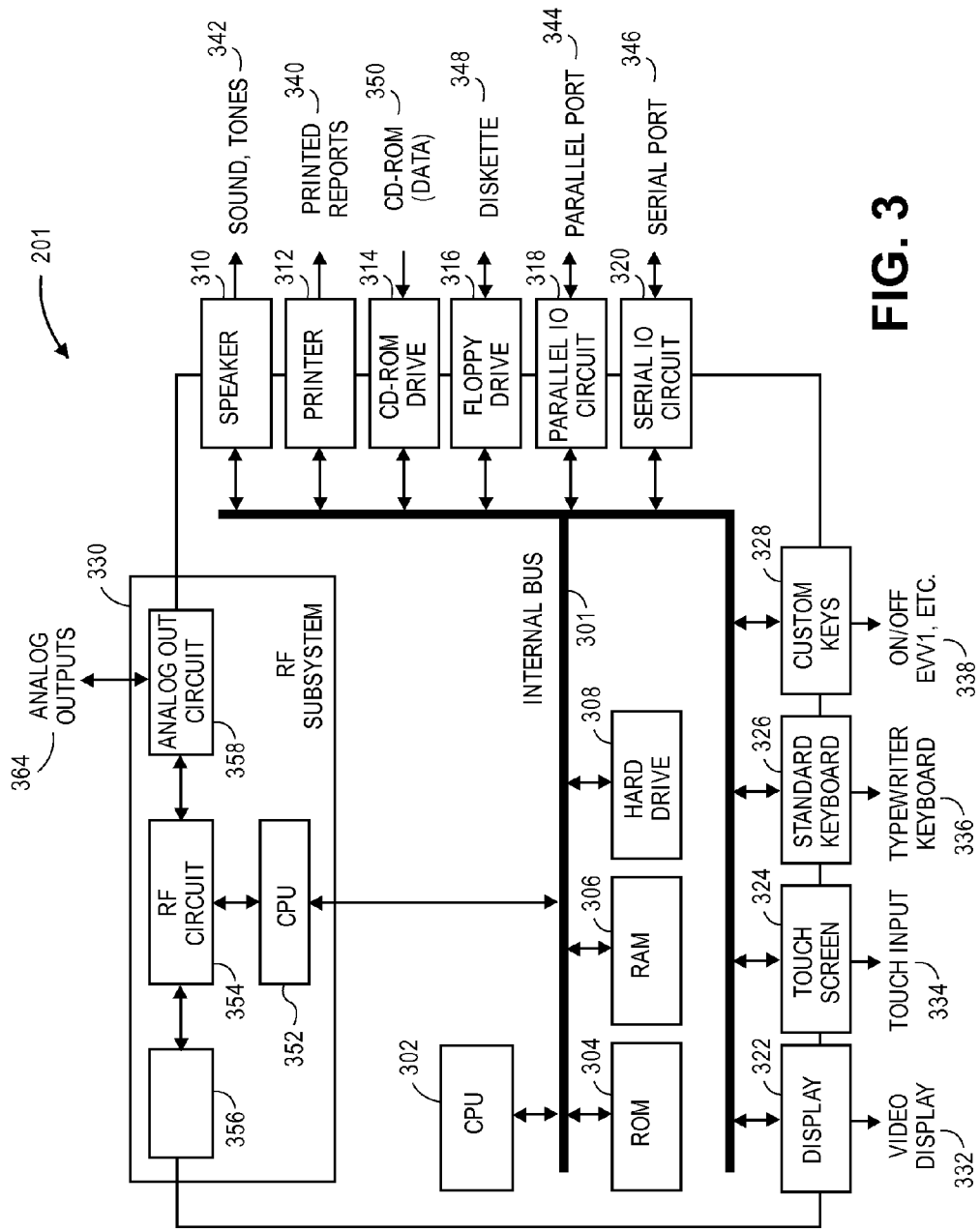
FIG. 3 illustrates a block diagram of exemplary internal components of an external device, according to an embodiment of the present disclosure.

FIG. 3 illustrates a functional block diagram of the external device 201 that is operated in accordance with the processes described herein and to interface with the IMD 101 as described herein. The external device 201 may be a workstation, a portable computer, a tablet computer, an IMD programmer, a PDA, a cell phone and/or the like located within a home of the patient 106, a hospital or clinic, an automobile, at an office of the patient, or the like.

The external device 201 may include an internal bus 301 that may connect/interface with a Central Processing Unit ("CPU") 302, ROM 304, RAM 306, a hard drive 308, a speaker 310, a printer 312, a CD-ROM drive 314, a floppy drive 316, a parallel I/O circuit 318, a serial I/O circuit 320, the display 322, a touchscreen 324, a standard keyboard 326, custom keys 328, and an RF subsystem 330. The internal bus 301 is an address/data bus that transfers information between the various components described herein. The hard drive 308 may store operational programs as well as data, such as stimulation waveform templates and detection thresholds.

The CPU 302 typically includes a microprocessor, a microcontroller, or equivalent control circuitry, designed specifically to control interfacing with the external device 201 and with the IMD 101. The CPU 302 may include RAM or ROM memory, logic and timing circuitry, state machine circuitry, and I/O circuitry to interface with the IMD 101. The display 322 (e.g., may be connected to the video display 332). The display 322 displays various information related to the processes described herein. The touchscreen 324 may display graphic information relating to the IMD 101 and include a graphical user interface. The graphical user interface may include graphical icons, scroll bars, buttons, and the like which may receive or detect user or touch inputs 334 for the external device 201 when selections are made by the user. Optionally the touchscreen 324 may be integrated with the display 322. The keyboard 326 (e.g., a typewriter keyboard 336) allows the user to enter data to the displayed fields, as well as interface with the RF subsystem 330. Furthermore, custom keys 328 turn on/off 338 (e.g., EVVI) the external device 201. The printer 312 prints copies of reports 340 for a physician to review or to be placed in a patient file, and the speaker 310 provides an audible warning (e.g., sounds and tones 342) to the user. The parallel I/O circuit 318 interfaces with a parallel port 344. The serial I/O circuit 320 interfaces with a serial port 346. The floppy drive 316 accepts diskettes 348. Optionally, the serial I/O port may be coupled to a USB port or other interface capable of communicating with a USB device such as a memory stick. The CD-ROM drive 314 accepts CD ROMs 350.

The RF subsystem 330 includes a central processing unit (CPU) 352 in electrical communication with an RF circuit 354, which may communicate with both memory 356 and an analog out circuit 358. The analog out circuit 358 includes communication circuits to communicate with analog outputs 364. The external device 201 may wirelessly communicate with the IMD 101 and utilize protocols, such as Bluetooth, BLE, ZigBee, MICS, and the like.

Figure 4:
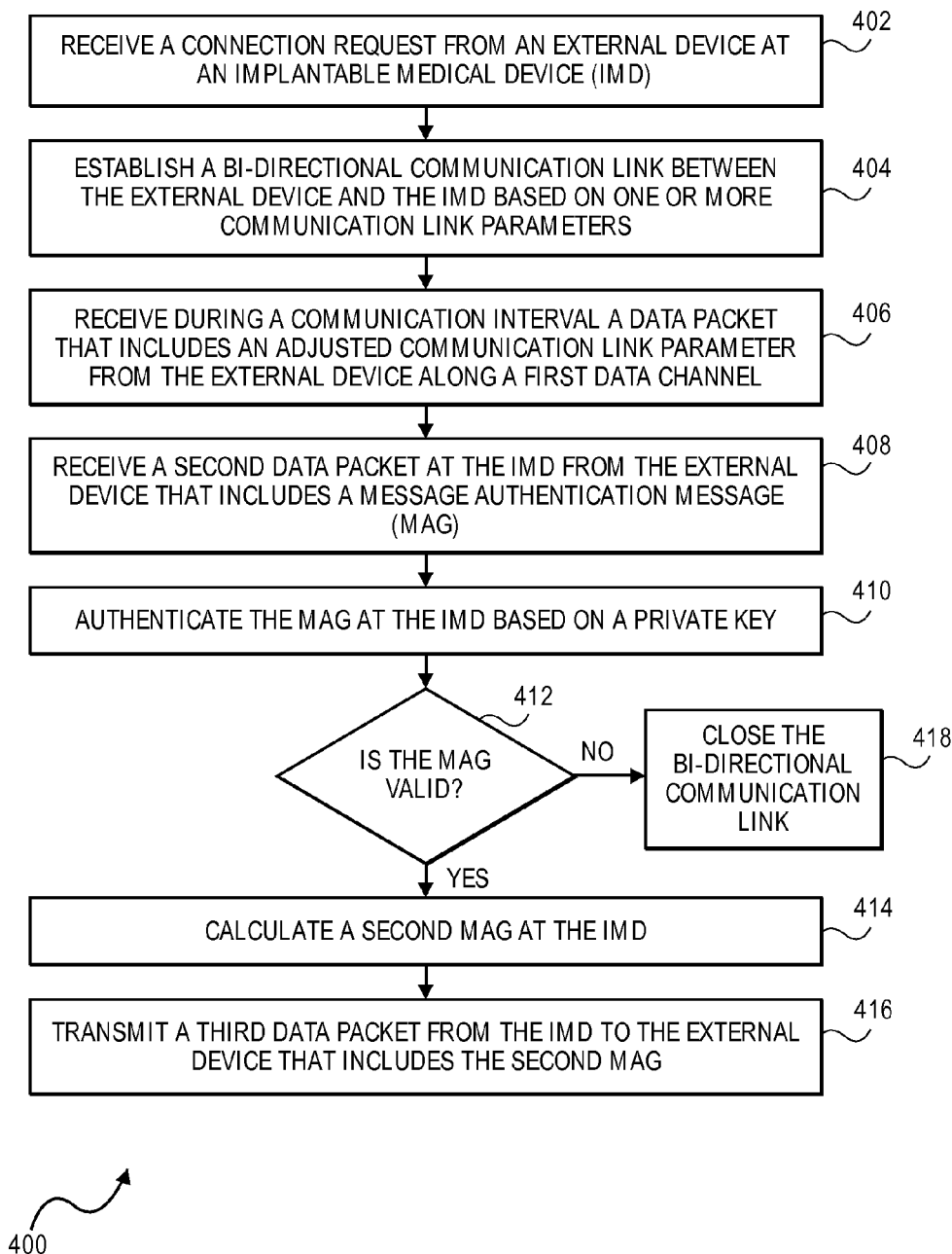
FIG. 4 illustrates a flowchart of a method for a secure bi-directional communication link between an external device and an implantable medical device.

FIG. 4 illustrates a flowchart of a method 400 for bridging a bi-directional communication link between an external device (e.g., 201) and an implantable medical device (IMD) (e.g., 101). The method 400 may be implemented as a software algorithm, package, or system that directs one or more hardware circuits or circuitry to perform the actions described herein. For example, the operations of the method 400 may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

At least one technical effect of at least one portion of the methods described herein includes i) receiving a connection request from an external device at an IMD, ii) establishing a bi-directional communication link between the external device and the IMD based on one or more communication link parameters, and iii) receiving during a communication interval a data packet that includes an adjusted communication link parameter from the external device along a first data channel.

Beginning at 402, a connection request is received from the external device 201 at the IMD 101. The connection request may be instructions included within a data packet transmitted from the external device 201 for establishing the bi-directional communication request. The connection request may include one or more communication link parameters based on the wireless protocol enabling the IMD 101 to establish a bi-directional communication link (e.g., 104) with the external device 201. The one or more communication link parameters may include a communication interval, frequency (e.g., data channel), address, timeout parameters, cyclic redundancy check, a data channel map, and/or the like.

The external device 201 may transmit the connection request along a dedicated frequency and/or frequency channels in response to an advertisement notice 505 (FIG. 5) transmitted from the IMD 101. For example, the wireless protocol may operate within a frequency range of 2400-2500 MHz. The wireless protocol may subdivide the frequency range into RF channels with a channel bandwidth (e.g., 2 MHz). The RF channels are allocated into two channel types, a data channel and an advertising channel. The data channel is used for communication between connected devices. The advertising channel is used by devices to discover new devices, initiate a connection, and broadcast data.

The operations of FIG. 4 will be described in connection with FIG. 5.

Figure 5:
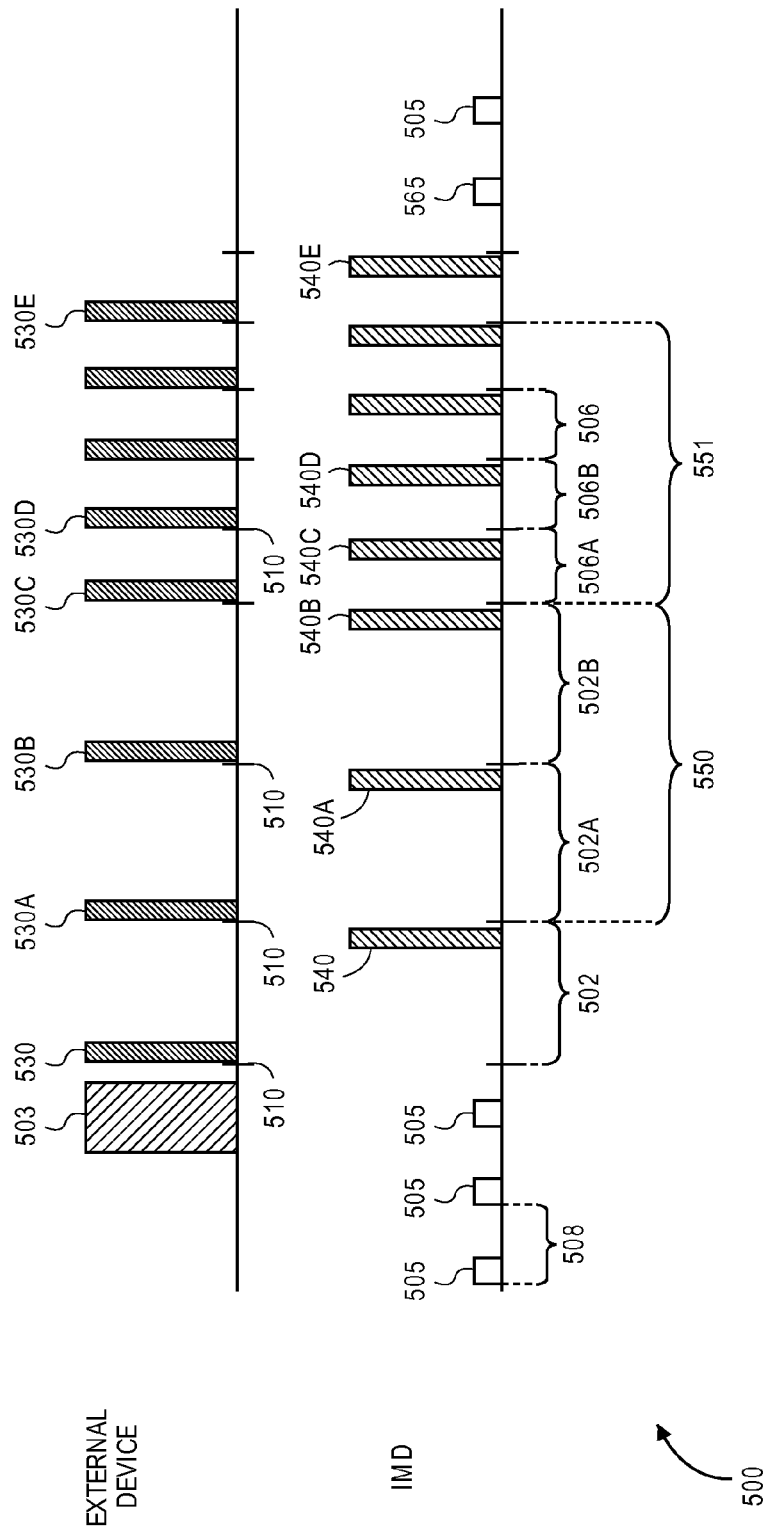
FIG. 5 illustrates a timing diagram of transmissions between an external device and an implantable medical device, according to an embodiment of the present disclosure.

FIG. 5 illustrates a timing diagram 500 of transmissions between the external device 201 and the IMD 101. The timing diagram 500 illustrates a series of advertisement notices 505 transmitted by the IMD 101 along one or more advertisement channels. The advertisement notice 505 represents a data packet that may contain frequency synchronization information utilized to form the bi-directional communication link 104, address information of the IMD 101, address information of the external device 201, and/or the like as defined by the wireless protocol. Additionally or alternatively, the advertisement notice 505 may include pairing and/or bondable information (e.g., passkey seed information). The advertisement notice 505 may be repeated, at a set or variable interval or an advertisement period 508, until the bi-directional communication link 104 is established. The advertisement period 508 represents a length of time between advertisement notices 505 transmitted by the IMD 101. The advertisement period may be predetermined and stored on memory 194.

The external device 201 monitors the one or more advertisement channels during a scanning interval 503 to detect one or more of the advertisement notices 505. The scanning interval 503 may be initiated by the user. For example, the user, using the touchscreen 324 or standard keyboard 336, may instruct the external device 201 to establish the bi-directional communication link 104. The CPU 302 (FIG. 3) of the external device 201 instructs the RF subsystem 330 to monitor one or more advertisement channels corresponding to the scanning interval 503. Optionally, the RF subsystem may repeat the scanning interval 503 every scan period. For example, the scan period represents a length of time between scan intervals. Optionally, the scanning interval 503 and/or scan period may be a predetermined length stored on the ROM 304, the RAM 306, or the hard drive 308. Optionally, the scanning interval 503 and/or scan period may be configured by the user, such that, the scanning interval 503 or scan period may be increased or decreased based on a user input received by the touchscreen 324 or standard keyboard 326. The RF subsystem 330 may continually repeat the scanning interval 503 until the CPU 302 acknowledges receipt of the advertisement notice 505.

The scan period and the advertisement period 508 occur independent and asynchronous with respect to one another, such that the advertisement notices 505 may intermittently overlap the scan intervals 503. Each period length is predetermined from distinct and separate sources. For example, the scan period is predetermined or configure by the user of the external device 201. Separately, the advertisement period 508 is predetermined by the protocol syntax stored in the memory 194. Optionally, one of the scan period or the advertisement period 508 may be altered, while, the length of the other period (e.g., advertisement period 508, scan period) remains constant.

Once the external device 201 receives the advertisement notice 505, in the form of a data packet transmitted from the IMD 101, the CPU 302 analyzes or compares the data packet with the protocol syntax stored on the ROM 304, the RAM 306, or the hard drive 308. The protocol syntax may include the structure of the advertisement notice (e.g., data packet specifications, appropriate number of bits, frequency, or the like) utilized by the wireless protocol. Optionally, the advertisement notice 505 may include a unique code designating the packet as an advertisement. By comparing the protocol syntax with the data packet, the CPU 302 determines whether the received data packet is an advertisement notice 505 using the wireless protocol of the external device 201. If the received data packet is determined not to be an advertisement notice, the external device 201 may continue scanning the advertisement channel. When the CPU 302 determines that the data packet received by the RF circuit 354 is the advertisement notice 505 (having the proper syntax), the CPU 302 outputs a connection request (e.g., within a payload of a data packet) to be transmitted by the RF circuit 354 along the advertisement channel.

The CPU 302 constructs a data packet representing the connection request by adding packet frames and/or a payload corresponding to the one or more communication link parameters such as the address of the IMD 101 and/or external device 201, error detection codes such as CRC, the communication interval 502, a frequency hopping increment, a data channel map, and/or the like. Additionally or alternatively, the payload may include connection instructions (e.g., frequency of the data channel for the bi-directional communication link 104) from the user intended for the IMD 101. When the data packet has been formed, the CPU 302 outputs the data packet to the RF subsystem 330 to be transmitted along the advertisement channel corresponding to the advertisement channel of the advertisement notice 505 transmitted from the IMD 101.

The communication interval 502 corresponds to a length of time for the exchange of data packets 530 and 540 between the IMD 101 and the external device. For example, the communication interval 502 may correspond to the length of time for the IMD 101 to respond to a data packet transmitted from the external device 201 over a select data channel. The communication interval 502 begins or starts at an anchor point 510. The anchor point 510 corresponds to when the external device 201 starts to transmit a data packet 530 to the IMD 101. Optionally, the communication interval 502 may be bounded by two consecutive data packets, one of which is transmitted from the external device and the other is transmitted from the IMD. For example, the communication interval 502 may be bounded by the data packet 530 and the data packet 540.

The data channel map may correspond to a subset of data channels of the RF channels defined by the wireless protocol. The data channels of the data channel map correspond to the one or more frequencies that can be used by the external device 201 and the IMD 101 for the bi-directional communication link 104 during one or more communication intervals 502. The data channels selected for the data channel map may be based on previous bi-directional communication links between the external device 201 and the IMD 101, data channels that are used by the external device 201 for alternative bi-directional communication links with other devices, and/or the like.

The frequency hopping increment may be an integer value (e.g., between 5 and 16), a list of data channels corresponding to an order of the data channel map, and/or the like used to determine a frequency hopping scheme of the IMD 101 and the external device 201. The frequency hopping scheme corresponds to an arrangement or order of select data channels of the data channel map used between the IMD 101 and the external device 201 during corresponding connection intervals 502. The frequency hopping scheme may be derived from a pre-defined hopping algorithm stored on the memory 194 of the IMD 101 and the ROM 304, RAM 306, and/or hard drive 308 of the external device 201. For example, the pre-defined hopping algorithm may determine the frequency hopping scheme based on the frequency hopping increment. By using the same frequency hopping increment, the same frequency hopping scheme may be determined from the pre-defined hopping algorithm separately by the IMD 101 and the external device 201. Based on the frequency hopping scheme, the RF circuits 110 and 354 continuously shift to the select data channels from the data channel map at the communication intervals 502 corresponding to the frequency hopping scheme.

For example, during the communication interval 502a, the RF circuits 110 and 354 may be at a select data channel of the bi-directional communication link 104. The select data channel is one of the data channels listed within the data channel map, and was determined from the pre-defined hopping algorithm based on the frequency hopping increment of the communication link parameter. The external device 201 and the IMD 101 exchange data packets 530a and 540a within the communication interval 502a over the select data channel during the connection interval 502a. Once the data packet 540a is transmitted from IMD 101, the RF circuit 110 may shift to a second data channel determined from the pre-defined hopping algorithm corresponding to the communication interval 502b. When the data packet 540a is received by the external device 201 indicating the end of the communication interval 502a, the RF circuit 354 of the external device 201 may shift to the second data channel for the communication interval 502b.

Returning to FIG. 4, at 404 the bi-directional communication link 104 is established between the external device 201 and the IMD 101 based on the one or more communication link parameters.

For example, the RF circuit 110 of the IMD 101 receives the data packet corresponding to the connection request. The RF circuit 110 may demodulate the RF signal and output the data packet to the microcontroller 160 via the interconnect 111. The microcontroller 160 may store the data packet on the memory 194 for analysis. The microcontroller 160 determines whether the data packet is in response to the advertisement notice 505 by comparing the address information of the data packet with the address information transmitted by the IMD 101 within the advertisement notice 505. If the address information matches, the microcontroller 160 partitions the payload from the data packet and carries out the instruction of the connection request from the payload by comparing the instructions to a stored instruction set on the memory 194 for the wireless protocol. Optionally, the microcontroller 160 may compare the address information of the external device 201 on the data packet with a permissible links table stored on the memory 194 to determine whether the connection request should be ignored by the IM 101 or partition the payload of the data packet.

When the microcontroller 160 identifies the connection request, the microcontroller 160 may instruct the RF circuit 110 to monitor the select data channel identified in the one or more communication link parameters for further instructions from the external device 201 within the communication interval 502, thereby establishing the bi-directional communication link 104. Additionally or alternatively, the external device 201 and the IMD 101 may initiate a pairing and/or bonding procedure as described in in U.S. patent application Ser. No. 14/091,809, entitled, "SYSTEM AND METHODS FOR ESTABLISHING A COMMUNICATION SESSION BETWEEN AN IMPLANTABLE MEDICAL DEVICE AND AN EXTERNAL DEVICE," which is expressly incorporated herein by reference.

At 406, during the communication interval 502b (FIG. 5) method 400 includes receiving the data packet 530b that includes an adjusted communication link parameter from the external device 201 along the first data channel. The adjusted communication link parameter may include a second communication interval 506. The second communication interval 506 may be different from the communication interval 502. For example, the second communication interval 506 may be shorter than the communication interval 502. In connection to FIG. 5, time intervals 550 and 551 correspond to a series of the communication intervals 502 and 506, respectively. The time intervals 550 and 551 are shown being approximately equal in length. However, approximately two communication intervals 502 occur during the time interval 550, and approximately four of the second communication intervals 506 occur during the time interval 551. It should be noted that in other embodiments, the second communication interval 506 may be longer than the communication interval 502.

Based on the second communication interval 506, the IMD 101 and the external device 201 may shift and/or hop data channels at a greater or more frequent rate than during the communication interval 502. For example, adjacent communication intervals, such as the communication intervals 502a and 502b or the second communication intervals 506a and 506b, may have different data channels based on the frequency hopping scheme. When the external device 201 and the IMD 101 adjust to the second communication interval 506, a greater number of the second communication intervals 506 occur during a time interval 551 corresponding to a greater number of shifts and/or changes in data channels relative to the communication interval 502.

The adjusted communication link parameter may be transmitted by external device 201 within the data packet 530b along the first data channel within the communication interval 502b. The first data channel may have been selected from the data channel map by the pre-defined hopping algorithm corresponding to the frequency hopping scheme. As described above, the adjusted communication link parameter may include the second communication interval 506. When the data packet 530b is received by the IMD 101, the IMD 101 may confirm receipt of the data packet 530b within the data packet 540b. Optionally, the adjusted communication link parameter may be transmitted in response to a request by the IMD 101. For example, the IMD 101 may include a request to adjust a communication link parameter within the data packet 540*a*.

Additionally or alternatively, the adjusted communication link parameter may include a second frequency hopping increment. The second frequency hopping increment may be different from the frequency hopping increment. For example, the second frequency hopping increment may be a different integer value relative to the frequency hopping increment. The second frequency hopping increment may be used by the IMD 101 and the external device 201 to adjust the frequency scheme based on the pre-defined hopping algorithm. For example, during the second communication interval 506*a* the data channel selected based on the second frequency hopping increment may be different than the data channel selected based on the first frequency hopping increment.

Returning to FIG. 4, optionally at 408, a second data packet 530*d* is received at the IMD 101 from the external device 201 that includes a message authentication guard (MAG). The MAG may be an encrypted string or series of characters within the payload and/or frame of the second data packet 530*d*. The MAG may be calculated by the external device 201 from a public key received from the IMD 101 and pre-defined criteria common and/or known to the IMD 101 and the external device 201.

Figure 6:
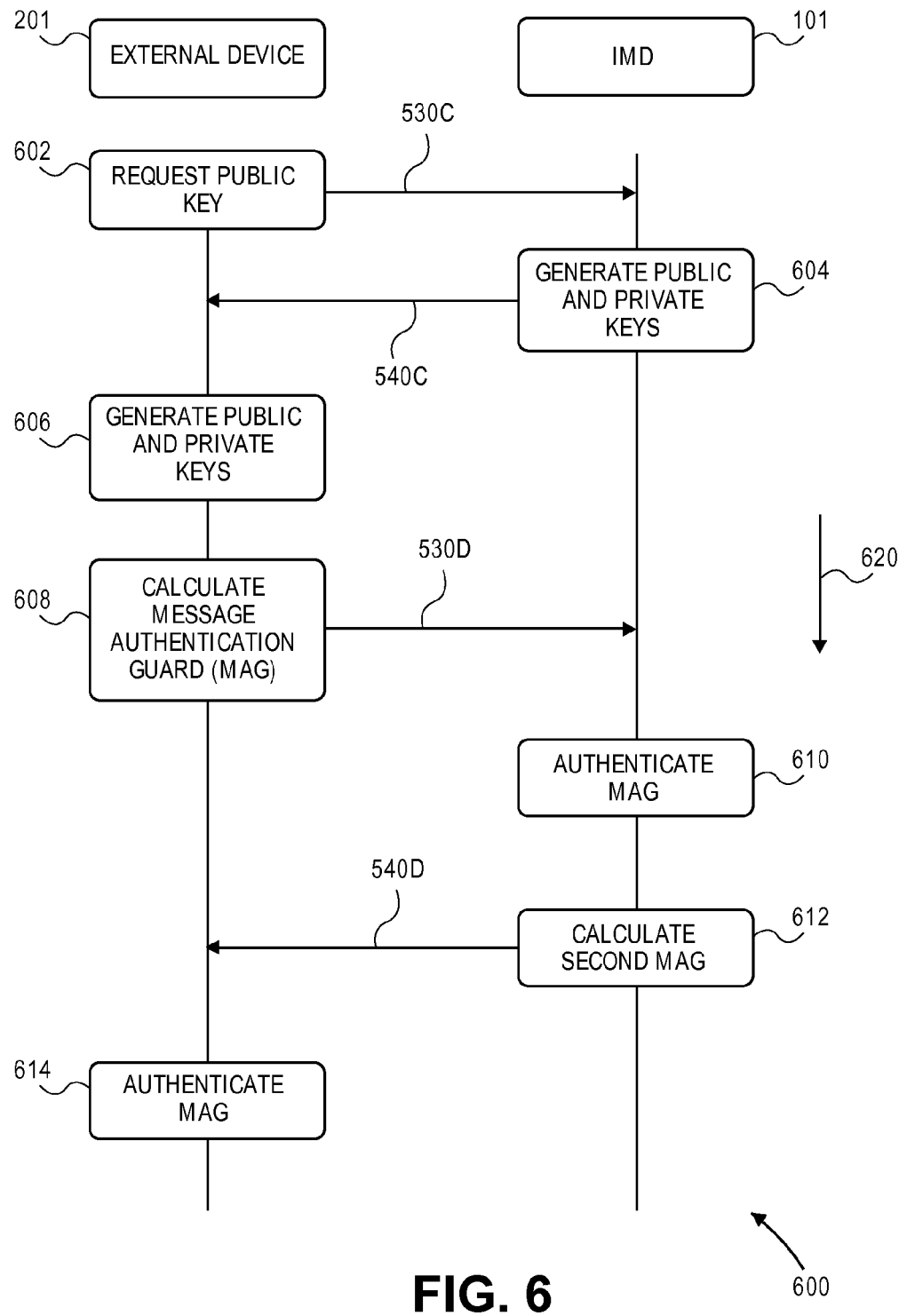
FIG. 6 illustrates a message sequence chart between an external device and an implantable medical device, according to an embodiment of the present disclosure.

FIG. 6 illustrates a message sequence chart 600 between the external device 201 and the IMD 101. The message sequence chart 600 illustrates the communications between the external device 201 and the IMD 101 over the bi-directional communication link 104 corresponding to, for example, the second communication intervals 506*a-b*. A vertical arrow 620 represents the progression of time.

The external device 201 may request at 602 a public key from the IMD 101. The request may be included within the data packet 530*c*. For example, the external device 201 may transmit the data packet 530*c* along the bi-directional communication link 104 via a second data channel corresponding to the communication interval 506*a* based on the frequency hopping scheme.

When the request for the public key is received by the IMD 101, at 604, the microcontroller 160 may generate the public key and a private key based on the pre-defined encryption algorithm stored on the memory 194. For example, the public key may be generated concurrently with or preceding to the generation of the private key by the microcontroller 160 using the pre-defined encryption algorithm. The public key and private key may be a string of characters that are mathematically linked by the pre-defined encryption algorithm based on, for example, an RSA algorithm standard. For example, the public key may be mathematically linked with the private key, such that a MAG calculated with the public key may be verified or decrypted with the private key. Similarly, in another example, a MAG calculated with the private key may be verified or decrypted with the public key. It should be noted, as described above, that the microcontroller 160 may generate the public key using the pre-defined encryption algorithm based on a private key stored on the memory 194.

When the private key is generated by the microcontroller 160, the IMD 101 may include the public key within the data packet 540*c*, and transmit the data packet 540*c* to the external device 201 along the bi-directional communication link 104 via the second data channel within the communication interval 506*a*. When the public key is received by the external device 201, the external device 201 may generate a public key and a private key at 606.

Optionally, the external device 201 may receive the private key and/or the public key from a remote server. For example, the external device 201 may send and/or transmit a request to a remote server. The request may include identification information of the IMD 101 based from the advertisement notice, the public key received from the IMD 101, a password or license key of the user using the external device 201, and/or the like. The password or license key may correspond to a user identification of rights and/or permission from the manufacturer of the IMD 101 to establish a bi-directional communication link with the IMD 101. When the remote server verifies the request from the external device 201, the remote server may send and/or transmit the public key to the external device 201. Optionally, the private key may be transmitted to the external device 201.

At 608, the external device 201 may calculate the MAG based on the private key received from the IMD 101 and the pre-defined criteria. For example, the external device 201 may encrypt the pre-defined criteria based on the public key using the pre-defined encryption algorithm to generate or calculate the MAG. The pre-defined criteria may be based on a time stamp, a static value, or a payload of the data packet 530*d* (e.g., a length of the payload) and is known by the IMD 101 and the external device 201. The payload of the data packet 530*d* may correspond to the public key of the external device 201 generated at 606.

When the MAG is generated by the external device 201, the external device 201 transmit the data packet 540*d* to the IMD 101 along the bi-directional communication link 104 via a third data channel within the communication interval 506*b* according to the frequency hopping scheme. It should be noted that the third data channel is a different RF channel than the second data channel.

The IMD 101 receives the data packet 530*d* from the external device 201 via the RF circuit 110. The data packet 530*d* includes the public key generated by the external device 201 and the MAG derived from the public key of the IMD 101 and the pre-defined criteria.

Returning to FIG. 4, at 410, the IMD 101 may authenticate the MAG based on the private key. For example, at 610 of FIG. 6, the IMD 101 may authenticate or verify the MAG or generally the data packet 530*d* based on the private key generated by the IMD 101 at 604. The microcontroller 160 may decrypt the MAG using the pre-defined encryption algorithm and the private key.

At 412, the IMD 101 may determine whether the MAG is valid. For example, when the MAG is decrypted, the microcontroller 160 may compare the decrypted MAG with the pre-defined criteria stored on the memory 194. The pre-defined criteria may correspond to a static value stored on the memory 194 of the IMD 101 and the ROM 304, the RAM 306, and/or the hard drive 308 of the external device 201. Thereby, the pre-defined criteria used for encrypting the MAG is common to the external device 201 and the IMD 101. The microprocessor 160 may verify or authenticate the decrypted MAG with the pre-defined criteria. If the decrypted MAG matches the pre-defined criteria, the microprocessor 160 may determine that the MAG of the data packet 530*d* or the data packet 530*d* is verified and/or authenticated.

In another example, the pre-defined criteria may correspond to a time stamp common to the external device 201 and the IMD 101. For example, the pre-defined criteria may correspond to the anchor point of the communication interval (e.g., the communication interval 502, the second communication interval 506), an amount of time from the connection request, and/or the like.

Additionally or alternatively, if the decrypted MAG does not match the pre-defined criteria, at 418, the microcontroller 160 may close the bi-directional communication link 104. For example, the microcontroller 160 may ignore data packets having address information corresponding to the external device 201. Optionally, the microcontroller 160 may instruct the RF circuit 110 to transmit advertisement notices 505 over one or more of the advertisement channels.

When the MAG is determined valid, at 414, the IMD 101 may calculate a second MAG. For example, the IMD 101 may partition the public key from the payload of the data packet 530*d*. At 612 of FIG. 6, the IMD 101 may generate or calculate the second MAG based on the partitioned public key from the external device 201 and the pre-defined criteria. The IMD 101 may encrypt the pre-defined criteria based on the public key using the pre-defined encryption algorithm to generate or calculate the second MAG. It should be noted that the second MAG may be different than the MAG generated by the external device 201 due to the different public keys. However, in at least one embodiment the second MAG and the MAG generated by the external device 201 may be approximately the same.

At 416, the IMD 101 may transmit the third data packet (e.g., the data packet 540*d*) to the external device 201 that includes the second MAG within the communication interval 506*b*. Optionally, the IMD 101 may include a confirmation within the payload indicating that the IMD 101 has authenticated or verified the MAG transmitted by the external device 201.

The external device 201 receives the data packet 540*d* from the IMD 101. At 614, the external device 201 may authenticate or verify the second MAG or generally the data packet 540*d* based on the private key generated by the external device 201 at 606. For example, the external device 201 may decrypt the second MAG using the pre-defined encryption algorithm and the private key.

When the second MAG is decrypted, the external device 201 may compare the decrypted second MAG with the pre-defined criteria stored on the ROM 304, the RAM 306, and/or the hard drive 308 (FIG. 3). The external device 201 may verify or authenticate the decrypted second MAG with the pre-defined criteria. If the decrypted second MAG matches the pre-defined criteria, the external device 201 may determine that the second MAG of the data packet 540*d* or the data packet 540*d* is verified and/or authenticated.

Additionally or alternatively, the external device 201 may transmit the data packet 540*d* to a remote server to authenticate and/or verify the second MAG. For example, the external device 201 may have the public key, but does not have the private key. The external device 201 may transmit all or a portion of the data packet 540*d*, such as the second MAG, to the remote server. The remote server may authenticate the second MAG using the private key and a pre-defined encryption algorithm by comparing the private key to the pre-defined criteria. Additionally or alternatively, the remote server may decrypt the second MAG and transmit and/or send the decrypted second MAG to the external device 201.

When the second MAG is determined valid, the external device 201 may transmit one or more instructions within one or more subsequent data packets 530 that include the MAG calculated from the public key received from the IMD 101. For example, the one or more instructions may correspond to measurement requests, programming instructions, status updates, and/or the like for the IMD 101.

The IMD 101 may determine and/or generate programmed responses within the payloads of one or more subsequent data packets 540 that include the second MAG in response to the one or more instructions received from the external device 201. The programmed responses may include measurements, status updates, confirmation responses, and/or the like.

Additionally or alternatively, the IMD 101 and/or the external device 201 may delete the received public keys and/or the generated public keys and/or private keys when the bi-directional communication link 104 is closed or terminated. For example, a termination request may be included in the data packet 530*e* from the external device 201. When the data packet 530*e* is transmitted by the RF circuit 354, the external device 201 may delete or remove the received public key from the IMD 101, the generated public key, and/or the generated private key.

The IMD 101 may receive the data packet 530*e* via the RF circuit 111. The microcontroller 160 may verify the termination request by comparing particular frames of the data packet (e.g., a header of the data packet), the payload of the data packet, and/or the like. When the microcontroller 160 verifies the termination request of the data packet 530*e*, the microcontroller 160 may terminate or close the bi-directional communication link 104, and may delete or remove the received public key from the external device 201, the generated public key, and/or the generated private key. After the bi-directional communication link 104 is terminated the IMD 101 may ignore data packets having address information corresponding to the external device 201. Optionally, the microcontroller 160 may instruct the RF circuit 111 to transmit a confirmation within a data packet 540*e* to the external device 201.

Additionally or alternatively, when the bi-directional communication link 104 has been terminated or closed, the IMD 101 may continually broadcast the one or more advertisement notices 505 over one or more advertisement channels.

It should be noted that in various embodiments the MAG may be static and/or the same for subsequent data packets 530 transmitted by the external device 201 after the data packet 530*d*. For example, the pre-defined criteria, such as the static value or time stamp, used to generate the MAG at 608 may not change for the subsequent data packets 530. Additionally or alternatively, the MAG generated by the external device 201 based on the pre-defined criteria may be dynamic or change. For example, the pre-defined criteria may be based on a dynamic value such as the payload of the data packets 530 attached to the MAG, an updating time stamp, and/or the like.

Optionally, the pre-defined criteria may be selected from a plurality of potential pre-defined criteria to generate a static or dynamic MAG based on an overall system performance of the IMD 101 and/or the external device 201. The overall system performance may correspond to a processing speed of the microcontroller 160 and/or CPU 302, capacity and/or charge of the battery 113 on the IMD 101, and/or the like. For example, an IMD having a low overall system performance may select the pre-defined criteria corresponding to a static MAG (e.g., a static value). In another example, an IMD having a higher overall system performance may select the pre-defined criteria corresponding to a dynamic MAG (e.g., based on the payload of the data packets).

It should be noted that although the message sequence chart 600 illustrates using an asymmetric cipher scheme based on a public key and a private key, in various other encryption schemes, such as a symmetric cipher scheme, may be used. For example, the IMD 101 may receive a security scheme request from the external device 201. The security scheme request may correspond to an instruction or request from the external device 201 to the IMD 101 on the type of cypher (e.g., symmetric, asymmetric) compatible with the IMD 101 for generating and/or authenticating the MAG. The type of cypher compatible with the IMD 101 may be based on the pre-defined encryption algorithm stored on the memory 194.

When the IMD 101 receives the security scheme request, the IMD 101 may transmit at least one of a public key or a static code to the external device 201 based on the compatible cypher of the IMD 101. For example, the public key may correspond to an asymmetric security scheme (e.g., at 604), and the static code may correspond to a symmetric security scheme. The static code may be a pre-determined series of characters stored on the memory 194 of the IMD 101 and the ROM 304, the RAM 306, and/or the hard drive 308 of the external device 201. The external device 201 may compare the static code received from the IMD 101 with the static code stored on the ROM 304, the RAM 306, and/or the hard drive 308.

If the two static codes match, the external device 201 may generate the MAG using the symmetric security scheme. For example, the IMD 101 and the external device 201 may each have a private key stored on the memory 194 of the IMD 101 and the ROM 304, the RAM 306, and/or the hard drive 308 of the external device 201. The private key may be used by the IMD 101 and the external device 201 to generate or calculate MAGs and decrypt MAGs received within a data packet (e.g., the data packet 530, the data packet 540).

Figure 7:
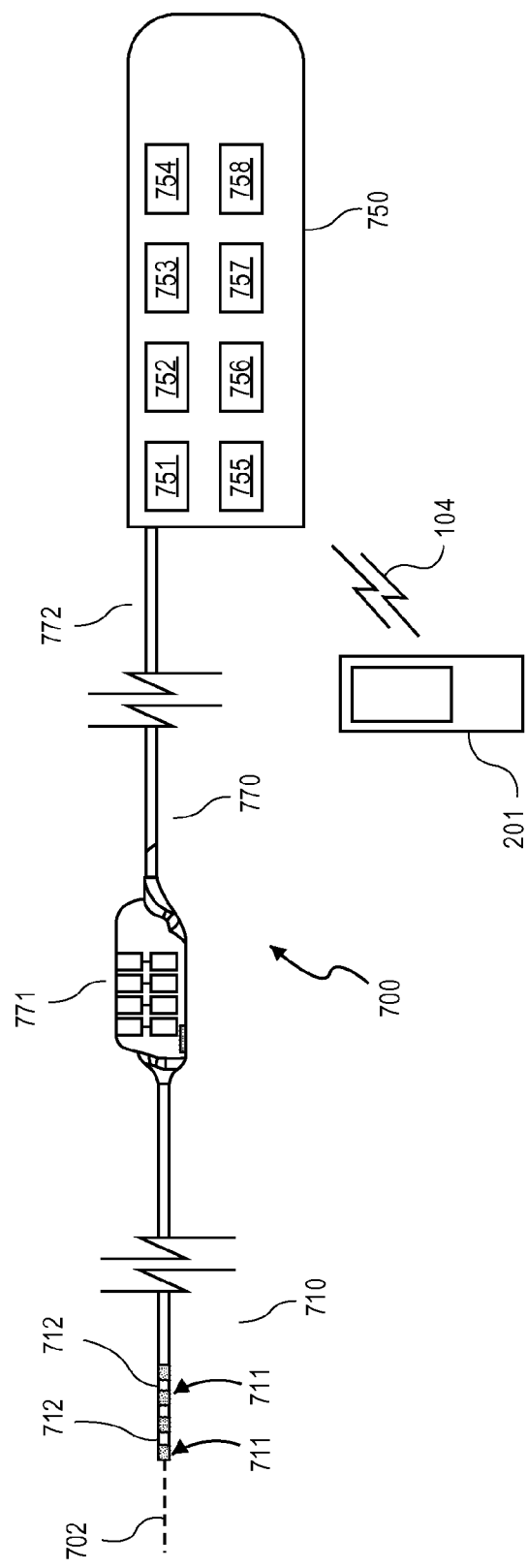
FIG. 7 illustrates a block diagram of exemplary internal components of an implantable medical device, according to an embodiment of the present disclosure.

FIG. 7 illustrates a block diagram of exemplary internal components of the IMD 700, in accordance with an embodiment. For example, the IMD 700 may be a neurostimulator adapted to stimulate spinal cord tissue, peripheral nerve tissue, deep brain tissue, cortical tissue, cardiac tissue, digestive tissue, pelvic floor tissue, or any other suitable nerve tissue of interest within a patient's body.

The IMD 700 may include an implantable pulse generator (IPG) 750 that is adapted to generate electrical pulses applied to the tissue of a patient. Additionally or alternatively, the IPG 750 may be an external neuro pulse generator. The IPG 750 typically comprises a metallic housing that encloses a controller 751, pulse generating circuitry 752, a charging coil 753, a battery 754, RF circuit 755, battery charging circuitry 756, switching circuitry 757, memory 758, and the like.

The controller 751 (also referred to herein as a processor module or unit) typically includes a microprocessor, or equivalent control circuitry, designed specifically for controlling the components of the IPG 750 and may further include RAM or ROM memory, logic and timing circuitry, state machine circuitry, and I/O circuitry. Typically, the controller 751 includes the ability to process or monitor input signals (data) as controlled by program code stored in memory. The details of the design and operation of the controller 751 are not critical to the invention. Rather, any suitable controller 751 may be used that carries out the functions described herein.

The IPG 750 may comprise a separate or an attached extension component 770. If the extension component 770 is a separate component, the extension component 770 may connect with a "header" portion of the IPG 750 as is known in the art. If the extension component 770 is integrated with the IPG 750, internal electrical connections may be made through respective conductive components. Within the IPG 750, electrical pulses are generated by the pulse generating circuitry 752 and are provided to the switching circuitry 757. The switching circuitry 757 connects to outputs of the IPG 750. Electrical connectors (e.g., "Bal-Seal" connectors) within the connector portion 771 of the extension component 770 or within the IPG header may be employed to conduct various stimulation pulses. The terminals of one or more leads 710 are inserted within connector portion 771 or within the IPG header for electrical connection with respective connectors. Thereby, the pulses originating from the IPG 750 are provided to the leads 710. The pulses are then conducted through the conductors of the lead 710 and applied to tissue of a patient via stimulation electrodes 711 that may be coupled to blocking capacitors. Any suitable known or later developed design may be employed for connector portion 771.

The stimulation electrodes 711 may be positioned along a horizontal axis 702 of the lead 710, and are angularly positioned about the horizontal axis 702 so the stimulation electrodes 711 do not overlap. The stimulation electrodes 711 may be in the shape of a ring such that each stimulation electrode 711 continuously covers the circumference of the exterior surface of the lead 710. Each of the stimulation electrodes 711 are separated by non-conducting rings 712, which electrically isolate each stimulation electrode 711 from an adjacent stimulation electrode 711. The non-conducting rings 712 may include one or more insulative materials and/or biocompatible materials to allow the lead 710 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 711 may be configured to emit the pulses in an outward radial direction proximate to or within a stimulation target. Additionally or alternatively, the stimulation electrodes 711 may be in the shape of a split or non-continuous ring such that the pulse may be directed in an outward radial direction adjacent to the stimulation electrodes 711. Examples of a fabrication process of the stimulation electrodes 711 is disclosed in U.S. Pat. No. 9,054,436, entitled "METHOD OF FABRICATING STIMULATION LEAD FOR APPLYING ELECTRICAL STIMULATION TO TISSUE OF A PATIENT," which is expressly incorporated herein by reference.

It should be noted the stimulation electrodes 711 may be in various other formations, for example, in a planar formation on a paddle structure as disclosed in U.S. patent application Ser. No. 14/198,260, entitled, "PADDLE LEADS FOR NEUROSTIMULATION AND METHOD OF DELIVERYING THE SAME," which is expressly incorporated herein by reference.

The lead 710 may comprise a lead body 772 of insulative material about a plurality of conductors within the material that extend from a proximal end of lead 710, proximate to the IPG 750, to its distal end. The conductors electrically couple a plurality of the stimulation electrodes 711 to a plurality of terminals (not shown) of the lead 710. The terminals are adapted to receive electrical pulses and the stimulation electrodes 711 are adapted to apply the pulses to the stimulation target of the patient. Also, sensing of physiological signals may occur through the stimulation electrodes 711, the conductors, and the terminals. It should be noted that although the lead 710 is depicted with four stimulation electrodes 711, the lead 710 may include any suitable number of stimulation electrodes 711 (e.g., less than four, more than four) as well as terminals, and internal conductors. Additionally or alternatively, various sensors (e.g., a position detector, a radiopaque fiducial) may be located near the distal end of the lead 710 and electrically coupled to terminals through conductors within the lead body 772.

For implementation of the components within the IPG 750, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 756) of an IPG 750 using inductive coupling and external charging circuits are described in U.S. Pat. No. 7,212,110, entitled "IMPLANTABLE DEVICE AND SYSTEM AND METHOD FOR WIRELESS COMMUNICATION," which is expressly incorporated herein by reference.

An example and discussion of "constant current" pulse generating circuitry (e.g., pulse generating circuitry 752) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 750. Different pulses on different stimulation electrodes 711 may be generated using a single set of the pulse generating circuitry 752 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various stimulation electrodes of one or more leads 711 as is also known in the art. Various sets of parameters may define the pulse characteristics and pulse timing for the pulses applied to the various stimulation electrodes 711 as is known in the art. Although constant current pulse generating circuitry is contemplated for some embodiments, any other suitable type of pulse generating circuitry may be employed such as constant voltage pulse generating circuitry.

The stimulation parameters (e.g., amplitude, frequency, type of stimulation waveform) and other operating parameters of the IMD 700 may be non-invasively programmed into the memory 758 through the RF circuit 755 in bi-directional wireless communication link 104. For example, the external device 201 may permit the user to move electrical stimulation along and/or across one or more of the lead(s) 710 using different stimulation electrode 711 combinations by communicating to the IMD 700, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference. The controller 751 controls the RF circuit 755 and receives data/transmissions from the RF circuit 755. The RF circuit 755 further allows status information relating to the operation of IMD 700 (as contained in the controller 751 or memory 758) to be sent to via the bi-directional communication link 104.

The controller 751 may support a particular wireless communication protocol while communicating with the external device 201, such as Bluetooth low energy, Bluetooth, ZigBee, Medical Implant Communication Service ("MICS"), or the like. Protocol firmware may be stored in memory 758, which is accessed by the controller 751. The protocol firmware provides the wireless protocol syntax for the controller 751 to assemble data packets, establish communication links 104, and partition data received from the bi-directional communication link 104.

The memory 758 may also contain a pre-defined algorithm that generates a passkey. The passkey may be used to initiate a bonding procedure between the IMD 700 and the external device 201 to establish a secured bi-directional communication session over the bi-directional communication link 104. The passkey may be generated based on a dynamic seed and/or a static identification received by the RF circuit 755 through the bi-directional communication link 104 from the external device 201 and inputted into the pre-defined algorithm. Optionally, the dynamic seed may be a random number generated by the controller 751, based on the local system clock of the IMD 700, or the like that is transmitted by the RF circuit 755 to the external device. Additionally or alternatively, the static identification may be stored on the memory 758 representing a product serial identification number of the IMD 700, which is a unique number assigned to the IMD 700 by a manufacturer of the IMD 700. Optionally, the static identification may be a pre-determined number stored on the memory 758 set by a user.

The controller 751, the microcontroller 160, and CPUs 302 and 352 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controller 751, the microcontroller 160, and CPUs 302 and 352 represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controller 751, the microcontroller 160, and CPUs 302 and 352 may execute a set of instructions that are stored in one or more storage elements, in order to process data. The storage elements may also store data or other information as desired or needed. The storage element may be in the form of an information source or a physical memory element within the controller 751, the microcontroller 160, and CPUs 302 and 352. The set of instructions may include various commands that instruct the controller 751, the microcontroller 160, and CPUs 302 and 352 to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A method for maintaining a bi-directional communication link between an external device and an implantable medical device (IMD), the method comprising:
    receiving a connection request from an external device at an IMD, wherein the communication request includes one or more communication link parameters based on a wireless protocol, the one or more communication link parameters defining a first communication interval;
    establishing a bi-directional communication link between the external device and the IMD based on the one or more communication link parameters; and
    receiving, during the first communication interval, a data packet from the external device along a first data channel, the data packet including an adjusted communication link parameter, wherein the adjusted communication link parameter includes a second communication interval having a length that is different from a length of the first communication interval.

2. The method of claim 1, wherein the second communication interval is bounded by two consecutive data packets, one of which is transmitted from the external device and the other is transmitted from the IMD.

3. The method of claim 1, further comprising shifting to a second data channel during the second communication interval, wherein the second data channel is selected based on the one or more communication link parameters.

4. The method of claim 1, further comprising transmitting, during the first communication interval, a second data packet from the IMD along the first data channel, wherein the first communication interval is bounded by the data packet and the second data packet.

5. The method of claim 1, further comprising:
    transmitting a first public key at the IMD to the external device; and
    receiving a second data packet at the IMD from the external device, wherein the second data packet includes a second public key and a message authentication guard derived from the first public key and a pre-defined criteria.

6. The method of claim 5, further comprising:
    authenticating the message authentication guard at the IMD based on a private key.

7. The method of claim 5, wherein the pre-defined criteria is based on at least one of a time stamp, a static value, or a payload of the second data packet.

8. The method of claim 5, further comprising:
    calculating a second message authentication guard based on the second public key and the pre-defined criteria; and
    transmitting a third data packet from the IMD to the external device, wherein the third data packet includes the second message authentication guard, wherein the second message authentication guard is different from the first authentication guard.

9. The method of claim 5, further comprising:
    deleting the first public key and the second public key when the bi-directional communication link is closed.

10. The method of claim 1, further comprising:
    receiving a second data packet at the external device from the IMD, wherein the second data packet includes a message authentication guard;
    authenticating the second data packet based on a private key.

11. The method of claim 10, further comprising:
    transmitting the second data packet from the external device to a remote server, wherein the authenticating operation is performed at the remote server.

12. The method of claim 1, further comprising:
    receiving a security scheme request at the IMD from the external device;
    transmitting from the IMD at least one of a public key or a static code to the external device, wherein the public key corresponds to a asymmetric security scheme and the static code corresponds to a symmetric security scheme.

13. The method of claim 1, wherein the one or more communication link parameters includes a frequency hopping increment, and the adjusted communication link parameter includes a second frequency hopping increment.

14. The method of claim 1, wherein the wireless protocol constitutes at least one of a Bluetooth protocol, a Bluetooth low energy protocol, or a ZigBee protocol.

15. A system for maintaining a bi-directional communication link comprising:
    an external device and an implantable medical device (IMD) configured to establish a bi-directional communication link there between over a wireless protocol, wherein the bi-directional communication link is based on one or more communication link parameters defining at least a first communication interval and a data channel map;

the IMD includes one or more processors electrically coupled to a radio frequency (RF) circuit and a memory module, the one or more processors are configured to:
continuously shift the RF circuit to select data channels from the data channel map based on the first communication interval; and
receive, during the first communication interval, an adjusted communication link parameter from the external device, wherein the adjusted communication link parameter includes a second communication interval having a length that is different from a length of the first communication interval.

16. The system of claim 15, wherein second communication interval is bounded by two consecutive data packets, one of which is transmitted from the external device and the other is transmitted from the IMD.

17. The system of claim 15, wherein the one or more processors are further configured to shift the RF circuit to a second data channel during the second communication interval, wherein the second data channel is selected based on the one or more communication link parameters.

18. The system of claim 15, wherein the one or more processors are further configured to:
transmit a first public key to the external device; and
receive a second data packet from the external device, wherein the second data packet includes a second public key and a message authentication guard derived from the first public key and a pre-defined criteria.

19. The system of claim 15, wherein the one or more processors are further configured to authenticate the message authentication guard based on a private key store on the memory module.

20. The system of claim 15, wherein the one or more processors are further configured to:
calculate a second message authentication guard based on the second public key and the pre-defined criteria; and
transmit a third data packet to the external device, wherein the third data packet includes the second message authentication guard, wherein the second message authentication guard is different from the first authentication guard.

* * * * *